(12) United States Patent
Kim

(10) Patent No.: US 11,653,836 B2
(45) Date of Patent: May 23, 2023

(54) CALORIE ESTIMATION APPARATUS AND METHOD, AND WEARABLE DEVICE

(71) Applicant: SAMSUNG ELECTRONICS CO., LTD., Suwon-si (KR)

(72) Inventor: Sang Kyu Kim, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 161 days.

(21) Appl. No.: 17/184,002

(22) Filed: Feb. 24, 2021

(65) Prior Publication Data

US 2021/0177264 A1 Jun. 17, 2021

Related U.S. Application Data

(62) Division of application No. 15/369,140, filed on Dec. 5, 2016, now Pat. No. 10,952,620.

(30) Foreign Application Priority Data

Jun. 16, 2016 (KR) .......................... 10-2016-0075240

(51) Int. Cl.
*A61B 5/00* (2006.01)
*A61B 5/145* (2006.01)

(52) U.S. Cl.
CPC ............ *A61B 5/0075* (2013.01); *A61B 5/441* (2013.01); *A61B 5/4866* (2013.01); *A61B 5/681* (2013.01);
(Continued)

(58) Field of Classification Search
CPC ..... A61B 5/0075; A61B 5/441; A61B 5/4866; A61B 5/681; A61B 5/7278; A61B 5/14532; A61B 5/6801; A63B 2220/836; A63B 2230/75; G16H 20/60; G16H 40/63; G01N 21/1717; G01N 33/02; G01N 2021/1742; G01J 3/28; G01J 2003/283; G01J 2003/2856
See application file for complete search history.

(56) References Cited

U.S. PATENT DOCUMENTS 6,126,595 A 10/2000 Amano et al.
8,808,628 B2 8/2014 Hanamatsu et al.
(Continued)

FOREIGN PATENT DOCUMENTS

JP 2005152258 A 6/2005
JP 201337648 A 2/2013
(Continued)

OTHER PUBLICATIONS

Katsuhiko Maruo et al., "Noninvasive Blood Glucose Assay Using a Newly Developed Near-Infrared System", IEEE Journal of Selected Topics in Quantum Electronics, vol. 9, No. 2, Mar./Apr. 2003, pp. 322-330.
(Continued)

*Primary Examiner* — Hien N Nguyen
(74) *Attorney, Agent, or Firm* — Sughrue Mion, PLLC

(57) ABSTRACT

A calorie estimation apparatus and method that analyze a user's skin spectrum to determine calories of food and drink that the user has ingested are provided. The calorie estimation apparatus includes a spectrum measurer configured to measure a skin spectrum of a user; and a processor configured to determine a noise of the measured skin spectrum, and estimate calories consumed by the user based on the determined noise.

3 Claims, 12 Drawing Sheets

(52) U.S. Cl.
CPC ........ *A61B 5/7278* (2013.01); *A61B 5/14532* (2013.01); *A63B 2220/836* (2013.01); *A63B 2230/75* (2013.01)

(56) References Cited

U.S. PATENT DOCUMENTS

| | | |
|---|---|---|
| 2014/0335490 A1 | 11/2014 | Baarman et al. |
| 2015/0148623 A1 | 5/2015 | Benaron |
| 2015/0148624 A1 | 5/2015 | Benaron |
| 2015/0148632 A1 | 5/2015 | Benaron |
| 2015/0148636 A1 | 5/2015 | Benaron |
| 2015/0204832 A1 | 7/2015 | Ochi et al. |
| 2016/0051189 A1 | 2/2016 | Lee et al. |
| 2016/0313241 A1 | 10/2016 | Ochi et al. |

FOREIGN PATENT DOCUMENTS

| | | | |
|---|---|---|---|
| JP | 2013191137 | A | 9/2013 |
| KR | 10-1991-0015917 | A | 9/1991 |
| KR | 10-1995-0001504 | A | 1/1995 |
| KR | 101136357 | B1 | 4/2012 |
| KR | 101226782 | B1 | 1/2013 |
| KR | 1020160007889 | A | 1/2016 |
| KR | 1020160022638 | A | 3/2016 |

OTHER PUBLICATIONS

Communication dated Mar. 28, 2023, issued by the Korean Intellectual Property Office in Korean Patent Application No. 10-2016-0075240.

CALORIE ESTIMATION APPARATUS AND METHOD, AND WEARABLE DEVICE

CROSS-REFERENCE TO RELATED APPLICATION(S)

This application is a divisional of U.S. application Ser. No. 15/369,140, filed Dec. 5, 2016 in the United States Patent and Trademark Office, which claims priority from Korean Patent Application No. 10-2016-0075240, filed on Jun. 16, 2016 in the Korean Intellectual Property Office, the entire disclosures of which are incorporated herein by reference in their entireties.

BACKGROUND

1. Field

Apparatuses and methods consistent with exemplary embodiments disclosed herein relate to a calorie estimation apparatus and method, and a wearable device with calorie estimation technology.

2. Description of the Related Art

Recently, due to a growing interest in health, a study of medical technologies is being actively carried out. Accordingly, in addition to medical devices being used in hospitals or examination institutions, small medical devices that individuals can carry, such as wearable devices, are being developed. In addition, a healthcare device that can measure calories of food and drink has been developed for individuals who are very interested in maintaining a diet. Generally, calorie measurement technology measures consumed calorie information based on an amount of activity by using an acceleration sensor, a heart rate sensor, etc. Also, a technology for measuring calories intake of food and drink is non-invasive, and may measure biomolecules, such as blood sugar, and estimate calories. However, when using such non-invasive calorie measuring techniques, it is not easy to measure desired biomolecules.

SUMMARY

According to an aspect of an exemplary embodiment, there is provided a calorie estimation apparatus including: a spectrum measurer configured to measure a skin spectrum of a user; and a processor configured to determine a noise of the measured skin spectrum, and estimate calories consumed by the user based on the determined noise.

The processor may be configured to determine a difference between the determined noise and a reference spectrum noise, and estimate the calories based on the determined difference between the determined noise and the reference spectrum noise.

The reference spectrum noise may include at least one of statistics regarding a noise of a spectrum on an empty stomach of the user and noises of spectrums on empty stomachs of a plurality of users.

The processor may be configured to estimate the calories based on the determined difference between the determined noise and the reference spectrum noise by using a correlation model correlating a predefined noise and calories.

The processor may be configured to estimate the calories by modifying the correlation model or the determined difference between the determined noise and the reference spectrum noise based on at least one of health condition information and calorie consumption information.

The health condition information may include information indicating at least one of past or present diseases, unusual constitution, and medication information; and the calorie consumption information comprises: between a starting point in time of food and drink ingestion and a point in time of calorie measurement, at least one of whether the user has exercised, an amount of exercise, an exercise duration, and a time interval between an end point of exercise and the point in time of calorie measurement.

The processor may be configured to determine statistics regarding a spectrum variation in one or more positions of the measured spectrum, and use the determined statistics as the noise of the measured skin spectrum.

The statistics regarding the spectrum variation may include at least one of root mean square (RMS) and standard deviation.

The spectrum measurer may be configured to measure the spectrum by radiating light to skin of the user and detecting spectral lines of the light that is reflected or scattered by the skin.

The light may include at least one of near-infrared light and mid-infrared light.

According to an aspect of another exemplary embodiment, there is provided a calorie estimation method including: measuring a skin spectrum of a user; determining a noise of the measured skin spectrum; and estimating calories consumed by the user based on the determined noise.

The estimating of the calories may include: determining a difference between the determined noise and a reference spectrum noise, and estimating the calories based on the determined difference between the determined noise and the reference spectrum noise.

The reference spectrum noise may include at least one of statistics regarding a noise of a spectrum on an empty stomach of the user and noises of spectrums on empty stomachs of a plurality of users.

The estimating of the calories may include: estimating calories corresponding to the determined difference between the determined noise and the reference spectrum noise by using a correlation model correlating a predefined noise and calories.

The estimating of the calories may include: estimating the calories by modifying the correlation model or the difference between the determined noise and the reference spectrum noise based on at least one of health condition information and calorie consumption information.

The determining of the noise may include: determining statistics regarding a spectrum variation in one or more positions of the measured spectrum, and using the determined statistics as the noise of the measured skin spectrum.

The measuring of the spectrum may include: measuring the spectrum by radiating light to the skin of the user and detecting spectral lines of the light that returns from the skin.

According to an aspect of another exemplary embodiment, there is provided a calorie estimation apparatus, including: a communicator configured to receive skin spectrum data of a user from a spectrum measurement device; and a processor configured to determine a noise of the received skin spectrum data, and estimate calories consumed by the user based on the determined noise.

The processor may be configured to determine a difference between the determined noise and a reference spectrum noise, and estimate the calories based on the determined difference between the determined noise and the reference spectrum noise.

The processor may be configured to estimate calories corresponding to the determined difference between the determined noise and the reference spectrum noise by using a correlation model correlating a predefined noise and calories.

The communicator may be configured to receive, from a calorie management device, at least one of the reference spectrum noise and the correlation model, which are used for estimating the calories.

The communicator may be configured to transmit calorie information, estimated by the processor, to a calorie management device so that the calorie management device trains the correlation model.

The calorie estimation apparatus may further include: a calorie database (DB) configured to manage calorie history information of the user; wherein the processor is configured to, in response to completing an estimation of the calories consumed by the user, update the calorie history information of the calorie DB based on the estimated calorie information.

The calorie estimation apparatus may further include: an interface configured to receive a calorie estimation request and information from the user, input the calorie estimation request and the information in the processor, and provide the user with calorie information estimated by the processor.

The interface may be configured to determine a level of the estimated calories according to a preset criterion, and provide the estimated calories to the user in a way that corresponds to the determined level.

According to an aspect of another exemplary embodiment, there is provided a wearable device including: a main body; a spectroscope that is included in the main body, the spectroscope being configured to radiate light to skin of a user, detect spectral lines of the light that is reflected or scattered from the skin, and measure a skin spectrum based on the detected spectral lines; and a processor configured to determine a noise of the measured skin spectrum and estimate calories consumed by the user based on the determined noise.

The processor may further be configured to determine a difference between the determined noise and a reference spectrum noise, and estimate the calories based on the determined difference between the determined noise and the reference spectrum noise.

The wearable device may further include: a communicator, which is included in the main body, and configured to communicate with a calorie management device so as to receive at least one of the reference spectrum noise and a correlation model to be used for estimating the calories.

The wearable device may further include: a display that is mounted on the main body so as to show a user the calories that are estimated by the processor.

Other features and aspects may be apparent from the following detailed description, the drawings, and the claims.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

Figure 1:
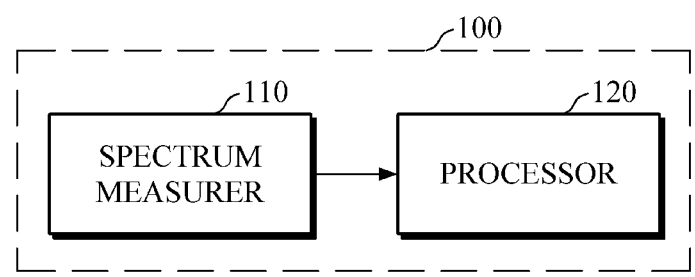
FIG. 1 is a diagram illustrating an example of a calorie estimation apparatus according to an exemplary embodiment.

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

The terms "first", "second", etc., may be used in the description of various elements, but the elements should not be limited by the terms. The terms are only used to distinguish one element from other elements. The expression of singularity includes the expression of plurality if the expression does not include a different meaning in the context of the expression. The description that one portion 'comprises' one element does not indicate that other elements are excluded, but instead indicates other elements may further be included unless indicated otherwise. In addition, the terms herein ". . . unit", "module", etc., may refer to a unit that processes at least one function or operation, and may be implemented in hardware or software, or in combination of hardware and software.

Throughout the drawings and the detailed description, unless otherwise described, the same drawing reference numerals will be understood to refer to the same elements, features, and structures. The relative size and depiction of these elements may be exaggerated for clarity, illustration, and convenience.

Hereinafter, specifically described are exemplary embodiments of a calorie estimation apparatus and method and a wearable device with reference to the corresponding figures.

FIG. 1 is a diagram illustrating an example of a calorie estimation apparatus according to an exemplary embodiment. A calorie estimation apparatus 100 according to an exemplary embodiment may be mounted on a wearable device a user can wear. The wearable device may be implemented as various types, e.g., a wrist watch type, a bracelet type, a wrist band type, a ring type, a glasses type, and a hairband type. Also, there is no specific limit to a form, size, or other characteristics of the wearable device.

Referring to FIG. 1, the calorie estimation apparatus 100 includes a spectrum measurer 110 and a processor 120.

The spectrum measurer 110 may measure a user's skin spectrum. According to an exemplary embodiment, the spectrum measurer 110 may measure the user's skin spectrum according to a predetermined control signal. The control signal may be generated by a control module that controls operations of the calorie estimation apparatus 100, and then transmitted to the spectrum measurer 110. The control module may be implemented as one function of the processor 120 that will be described later, but there is no limit thereto.

For example, the spectrum measurer 110 may radiate light to a user's skin and disperse the light coming back from the user's skin, thereby acquiring spectrum data. According to an exemplary embodiment, near-infrared ray (NIR), infrared spectroscopy using mid-infrared ray (MIR), Raman spectroscopy, or the like may be used.

A user's skin, on which light is irradiated, may be an area that is near the radial artery under the surface of wrist. The skin area where the radial artery exists may be comparatively less affected by external factors that make errors in measurement, such as the thickness of a skin tissue inside the wrist. However, the area of skin being measured is not limited thereto. The area where the light is irradiated may be peripheral parts of the human body, such as a finger, toe, or an earlobe, which is the part where a blood vessel density is high inside the human body.

When the measurement of the user's skin spectrum is started, the processor 120 may analyze the measured spectrum, thereby measuring a user's calories. For example, the processor 120 may measure a user's calories in the first condition based on the spectrums measured in the first condition and second condition, as specifically described below.

The first condition refers to a user's condition at the point in time when the user wants to measure the calories. For example, the first condition may be variously defined as: a condition in which a user has had food and drink; a condition in which after a user has had food and drink, a certain amount of time has passed; a condition in which after having food and drink, the user has exercised; a condition in which the user has exercised on an empty stomach, and the like. Also, the second condition refers to a reference condition for comparison with the spectrum measured in the first condition. For example, the second condition may be a condition of an empty stomach or a condition after a predetermined type and amount of food and drink have been ingested. However, the first and second conditions are not limited thereto, and the first and second conditions may be variously defined so as to be proper for criteria that is able to be applied in common to all the users or for a user's individual characteristics.

The processor 120 may generate a control signal for spectrum measurement by receiving a user's calorie estimation request. Also, the processor 120 may transmit the generated control signal to the spectrum measurer 110 and control the spectrum measurer 110 to measure a spectrum.

Figure 2A:
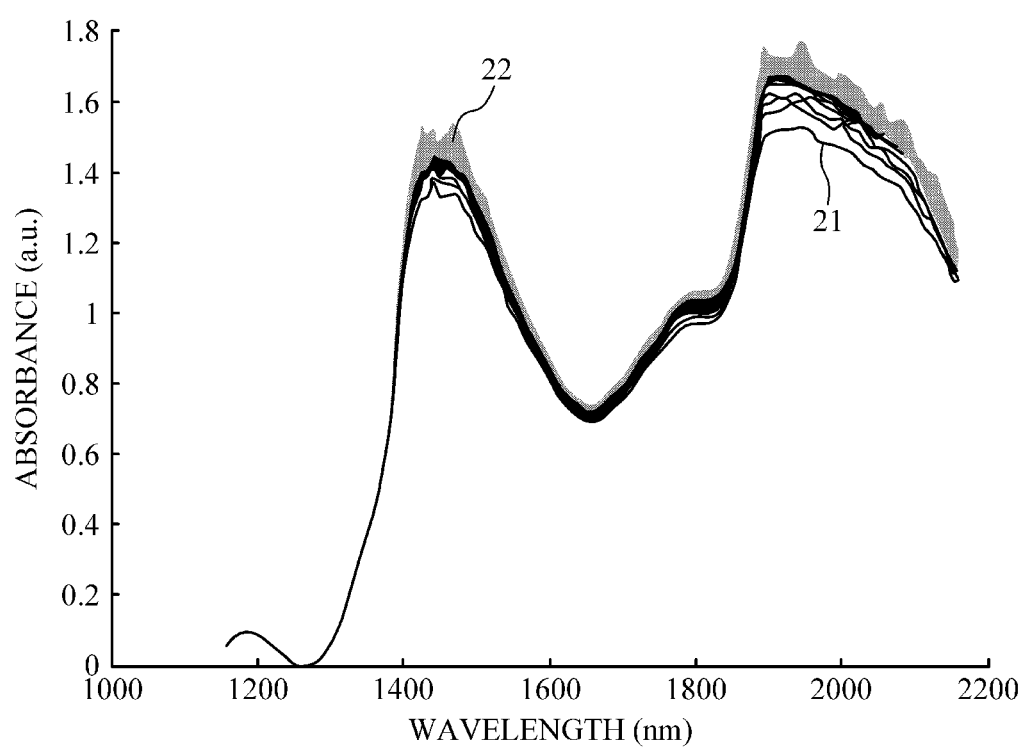
FIGS. 2A and 2B are diagrams illustrating examples of spectrums, which are measured in a condition of an empty stomach and after the ingestion of food and drink.
Figure 2B:
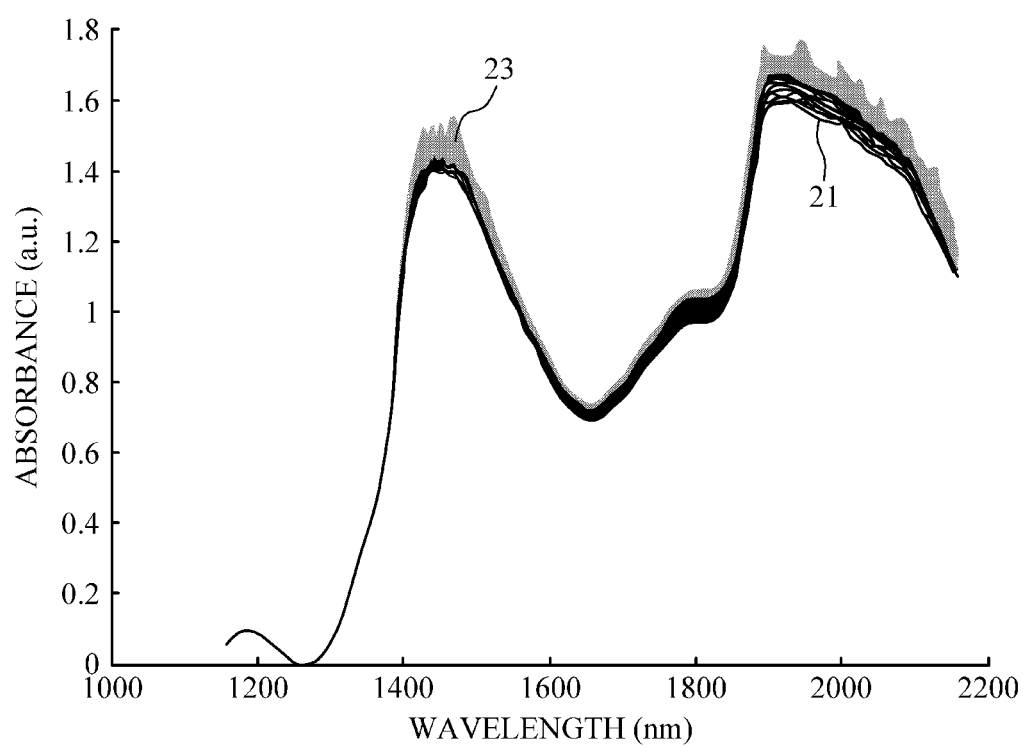

FIGS. 2A and 2B are diagrams illustrating examples of spectrums, which are measured in a condition of an empty stomach and after the ingestion of food and drink.

Specifically, FIG. 2A illustrates a spectrum 21 measured in a condition of an empty stomach, and a spectrum 22 measured after 75 g of glucose is ingested. Also, FIG. 2B illustrates a spectrum 21 measured in a condition of an empty stomach, and a spectrum 23 measured after a sweet red bean jelly (also referred to as Yang-gaeng) (carbohydrate 37 g and sugar 28 g) and juice (carbohydrate 30 g and sugar 22 g) have been ingested.

As illustrated in FIGS. 2A and 2B, the spectrum noises 22 and 23 at the time when food and drink, such as juice, are ingested, are bigger than the noise of the spectrum that is acquired after the skin spectrum 21 in a condition of an empty stomach is successively measured and calculated. This is because after the sugar, carbohydrate, etc., included in food and drink are digested, the ingested items make a small change in the skin, thereby increasing a noise of the spectrum.

Table 1 below is an example of noise changes in a spectrum in a condition of an empty stomach and a spectrum after food and drink have been ingested, as illustrated in FIGS. 2A and 2B.

TABLE 1

| | Ingested food | | | |
|---|---|---|---|---|
| | Glucose 75 g | | Yang-gaeng: carbohydrate 37 g, sugar 28 g Juice: carbohydrate 30 g, sugar 22 g | |
| Calories | 277.5 kcal | | 285 kcal (155 kcal + 130 kcal) | |
| Condition | Empty stomach | Ingested | Empty stomach | Ingested |
| Noise | 13900 µAU | 16600 µAU | 15600 µAU | 19700 µAU |
| Noise change | 2700 µAU | | 4100 µAU | |

As shown in Table 1, after a user has had the food and drink, if the digested food and drink, such as blood sugar, etc., flow in blood or is applied to the skin, a subtle change in a spectrum of the skin is generated. Referring to Table 1, when 75 g of glucose is ingested, the normal calories are 277.5 kcal. In this case, the spectrum noise measured in a condition of an empty stomach and the noise, measured after the glucose 75 g is ingested, are 13900 µAU and 16600 µAU, respectively, which makes a difference of 2700 µAU therebetween. Also, the normal calories when Yang-gaeng and juice are ingested are 285 kcal. In this case, the spectrum noise measured in a condition of an empty stomach, and the noise measured after food and drink are ingested, are 15600 µAU and 19700 µAU, respectively, which makes a difference of 4100 µAU therebetween.

As such, there may be a certain correlation between calories of ingested food and a change in the measured spectrum noise. The processor 120 may estimate calories of the food ingested by using the correlation between the spectrum noise and the calories, as described later with reference to FIGS. 3 to 11.

Figure 3:
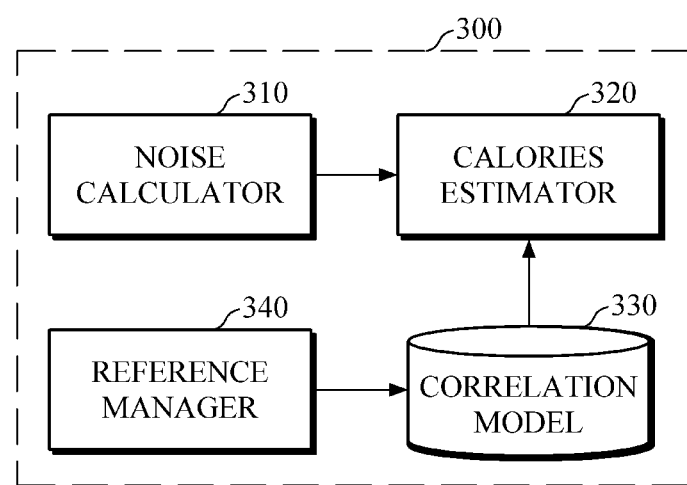
FIG. 3 is a detailed diagram illustrating a processor in FIG. 1 according to an exemplary embodiment.
Figure 4:
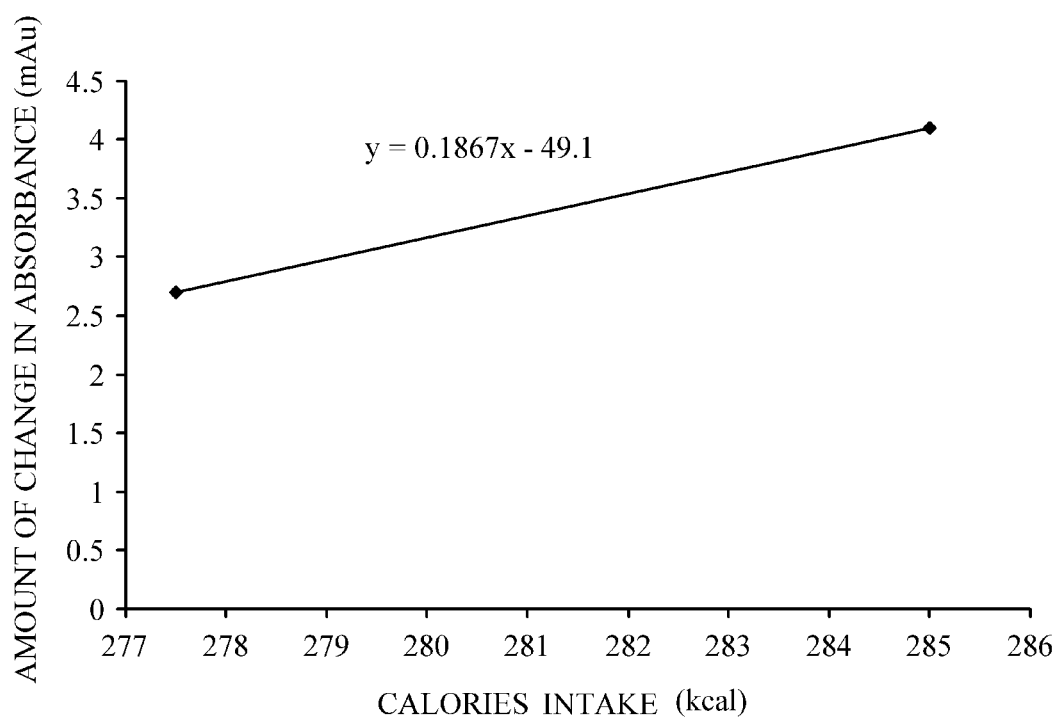
FIG. 4 is an example of a correlation model being used in calorie estimation.

FIG. 3 is a detailed diagram illustrating a processor in FIG. 1 according to an exemplary embodiment. FIG. 4 is an example of a correlation model being used in calorie estimation.

Referring to FIG. 3, the processor 300 may include a noise calculator 310, a calorie estimator 320, a correlation model 330, and a reference manager 340.

When a skin spectrum of a user is measured in the first condition, the noise calculator 310 may calculate (e.g., determine) a noise of the measured spectrum. The noise calculator 310 may calculate a variation of the spectrum in a plurality of wavelength positions of the measured spectrum, and use statistics regarding each of the calculated variations as a noise of the measured spectrum. According to an exemplary embodiment, the statistics may be based on root mean square (RMS) or standard deviation, but are not limited thereto.

For example, referring to FIG. 2A, the noise calculator 310 may select a plurality of wavelength positions in a wavelength range (1000 nm~2200 nm) of a continuous spectrum that is measured in a condition in which a user has ingested 75 g of glucose. Also, when the plurality of wavelength positions is selected, the noise calculator 310 may calculate a variation of the spectrum in each selected position. Also, the noise calculator 310 may calculate the root mean square (RMS) value of the variation of the spectrum in each calculated position, and accordingly may calculate, for example, 16600 μAU that is shown in Table 1 above as a noise of the spectrum after the glucose is ingested. According to an exemplary embodiment, the noise calculator 310 may regularly select the plurality of wavelength positions from the entire wavelength range (1000 nm~2200 nm). Alternatively, the plurality of wavelength positions may be selected relatively more frequently from a wavelength range that includes a big change in the spectrum, e.g., near 1400 nm, and from a range between 2000 nm and 2200 nm.

When the noise regarding the spectrum measured in the first condition by the noise calculator 310 is calculated, the calorie estimator 320 may estimate calories of the first condition by using the calculated spectrum noise of the first condition.

For example, the calorie estimator 320 may calculate the difference between the spectrum noise of the first condition and the reference spectrum noise of the second condition. Also, the calorie estimator 320 may estimate the calories of the first condition based on the calculated difference between the spectrum noises of the first and second conditions. According to an exemplary embodiment, the reference spectrum noise may be a noise of a reference spectrum that is measured in the second condition, e.g., in a condition of an empty stomach.

For example, the reference spectrum noise may be a noise of a continuous spectrum that is measured by a user who wants to estimate calories in a second condition. In another example, after spectrums of one user or two or more users are selected among the spectrums that are measured by other users in the second condition, the reference spectrum noise may be a noise that is calculated from the selected spectrums. According to an exemplary embodiment, in a case where the spectrums of a plurality of users are selected as reference spectrums, the statistics (e.g., average) of the noises that are calculated from the spectrum of each user may be used as a reference spectrum noise.

The calorie estimator 320 may estimate calories corresponding to a difference between a spectrum noise of the first condition and a reference spectrum noise of the second condition by applying a predefined correlation model. The correlation model may, for example, be installed in a calorie estimation apparatus in advance in the form of an equation algorithm, as illustrated in FIG. 4, which shows a correlation between an absorbance variation and calories. According to an exemplary embodiment, the absorbance variation may refer to a difference between spectrum noises measured in the first and second conditions.

In this case, when the difference between the spectrum noises in the first and second conditions is calculated, the calorie estimator 320 may run the pre-installed equation algorithm, put 2.7 mAU in the run equation algorithm, and acquire estimation calories of 277.45 kcal as a result thereof.

In another example, the correlation model may be stored in advance in a storage device in the form of a table, in which an absorbance variation and calories are matched. According to an exemplary embodiment, the storage device may include at least one type of the following storage media: a flash memory type, a hard disk type, a multimedia card micro type, and a card type (e.g., SD or XD memory, etc.), random access memory (RAM), static random access memory (SRAM), read only memory (ROM), electrically erasable programmable read only memory (EEPROM), programmable read only memory (PROM), magnetic memory, a magnetic disk, an optical disk, etc.

TABLE 2

| Absorbance variation (mAu) | Calorie intake (kcal) |
|---|---|
| 2.5~3.0 | 278 |
| 3.0~3.5 | 280 |
| 3.5~4.0 | 284 |
| . . . | . . . |

For example, referring to Tables 1 and 2, in a case where a difference between the noise of the spectrum measured in the first condition and the noise of the reference spectrum in the second condition is calculated to be 2700 μAU, the calorie estimator 320 may estimate the calorie intake to be 278 kcal.

The reference manager 340 may manage information that is a reference for calorie estimation, such as a noise of a reference spectrum and a correlation model.

For example, in order to acquire a user's reference spectrum noise, the reference manager 340 may control the spectrum estimator 110 and the noise calculator 310 to measure a spectrum from the user in the second condition, e.g., on an empty stomach, and calculate the noise from the measured spectrum. When the reference spectrum noise is calculated, the reference manager 340 may store the reference spectrum noise in a storage device and manage the reference spectrum noise.

In addition, in case where the correlation model needs to be updated, the reference manager 340 may control the spectrum measurer 110 and the noise calculator 310 to measure the spectrum and calculate the noise in the first condition, e.g., after a user has ingested various food and drink, whose calories are already known. As such, if the noise of the spectrum is calculated in the first condition, the reference manager 340 may update the correlation model by again acquiring the correlation with the calories based on the spectrum noise.

Furthermore, in order to adaptively respond to various changes in the situation, such as a user's change in the health condition, the reference manager 340 may manage update periods of a user's reference spectrum noise or a correlation model. According to an exemplary embodiment, the update periods may be set periodically and may be adjusted according to a user's input.

According to an exemplary embodiment, if there is a plurality of users using a calorie estimation apparatus 100, it is possible to manage the noise of the reference spectrum or the correlation model separately according to each of the plurality of users.

Figure 5:
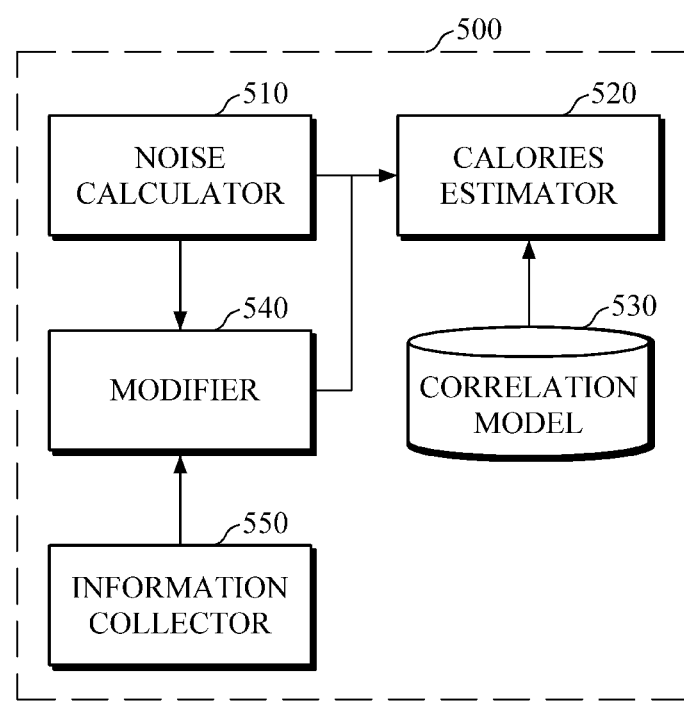
FIG. 5 is a detailed diagram illustrating a processor in FIG. 1 according to another exemplary embodiment.

FIG. 5 is a detailed diagram illustrating a processor in FIG. 1 according to another exemplary embodiment.

Referring to FIG. 5, a processor 500 may include a noise calculator 510, a calorie estimator 520, a correlation model 530, a modifier 540, and an information collector 550.

If the spectrum measurer 110 in FIG. 1 measures a user's skin spectrum in a first condition, in which a user wants to estimate calories, the noise calculator 510 may analyze the measured skin spectrum, thereby calculating a change of the spectrum, e.g., a noise. According to an exemplary embodiment, the noise calculator 510 may acquire the root mean square (RMS) or the standard deviation of the spectrum variation in a plurality of positions of the measured spectrum wavelength, and accordingly use the result thereof as a noise of the spectrum.

If the spectrum noise in a first condition is calculated by the noise calculator 510, the calorie estimator 520 may calculate a difference between the calculated spectrum noise and a reference spectrum noise of the second condition. Also, the calorie estimator 20 may estimate calories corresponding to the calculated difference between noises of both spectrums by using a correlation model 530.

According to an exemplary embodiment, the correlation model 530 may be an equation algorithm that shows a correlation between a noise difference of the spectrum and ingested calories, or may be a matching table, but the correlation model 530 is not limited to any particular type.

The information collector 550 may receive a user's calorie estimation request, which is transmitted from a control module that controls operations of the calorie estimation apparatus 100. Also, if the calorie estimation request is received, the information collector 550 may collect various types of information, which may affect calories, from the user through an interface module interfacing with the user in order to provide more accurate calorie information to the user. According to an exemplary embodiment, the control module and the interface module may be implemented in hardware or software so as to be performed in one unit or separately divided units, thereby being mounted on the calorie estimation apparatus 100 or connected wired/wirelessly.

Normally, each of the users may show a different calorie absorption even though users ingest food and drink having the same calories, due to various factors, such as loss of taste or smell caused by a physical change with aging, an individual's malfunction in absorption and metabolism, a physical dysfunction due to chronic diseases, loss of appetite due to medication, and a digestive dysfunction. In addition, if the users exercise after ingesting food and drink, the calorie consumption may be different according to the exercise duration, exercise intensity, etc. Due to this variance, it is difficult to provide accurate calorie information to a user even when the user wants to know calories of food and drink he or she has actually ingested.

The information collector 550 may collect a user's health condition information or calorie consumption information, etc., in order to estimate such calories that the user has actually ingested. According to an exemplary embodiment, the user's health condition information may include various types of information that may affect ingested calories, such as a user's age, sex, past, diseases, unusual constitution, and current medication information. In addition, the calorie consumption information may include various types of information that may affect calorie consumption, such as whether a user has exercised after having food and drink, an exercise duration, an amount of exercise, an exercise intensity, a time interval between an end point in time of exercise and a point in time when calories is measured, and the like.

If health condition information or calorie consumption information is collected from the user, the modifier 540 may modify a correlation model, spectrum noise information, estimated calorie information, etc., which are needed for estimating calories, by using the collected information.

For example, the modifier 540 may check whether a user has long-term factors that affect calories, such as a metabolic disorder or chronic diseases, by analyzing a user's health condition information. In response to the check indicating that the user has the long-term factors affecting the calories, the modifier 540 may determine that a correlation model needs to be modified, and may perform a modification of the correlation model in consideration of a difference between calories of the food and drink the user has actually ingested and calories absorbed in a user's body. The modification of the correlation model may be performed according to a user's request or a determination of the modifier 540 at a point in time when the calorie estimation apparatus 100 is initially used, or wherever a user's health condition is changed.

After determining that the correlation model needs to be modified, the modifier 540 may collect, from a user, learning data that is required for the modification of the correlation model, and train the existing correlation model by using the collected learning data, thereby modifying the correlation model. For example, the modifier 540 may induce a user to ingest food and drink with calories that are already known during a predetermined duration (e.g., a few hours, a day, a week, etc.). In addition, the modifier 540 may collect the actual ingested calorie information from the user, and may, as the learning data, collect the actual calorie information that has been collected and calorie information after the ingestion of food and drink, which is estimated by the noise calculator 510 and the calorie estimator 520.

In another example, the modifier 540 may analyze a user's calorie consumption information, thereby calculating calories that are consumed through exercise, etc., after the user ingests food and drink. In addition, if a user's calorie is estimated by the calorie estimator 520, the modifier 540 may modify the estimated calorie itself by using the calculated consumption calorie information. For example, if the estimated calories are 187 kcal, and the calories that the user has consumed are 100 kcal, the modifier 540 may acquire calorie information of 287 kcal, which the user has actually ingested, through a calorie modification.

The exemplary embodiments of the modifier 540 are not limited to the description above, and may modify a correlation model or estimated calories in consideration of a user's health condition information, calorie consumption information, etc. In addition, if necessary, the modifier 540 may modify a difference between noises of a spectrum of a first condition and a reference spectrum of a second condition.

The calorie estimation apparatus 100 according to exemplary embodiments described herein may provide estimated calorie information to a user through an interface module. According to an exemplary embodiment, if the calories are modified, the calorie estimation apparatus 100 may provide a user with the estimated calorie information before the modification and the calorie information that is estimated through the modification.

Figure 6:
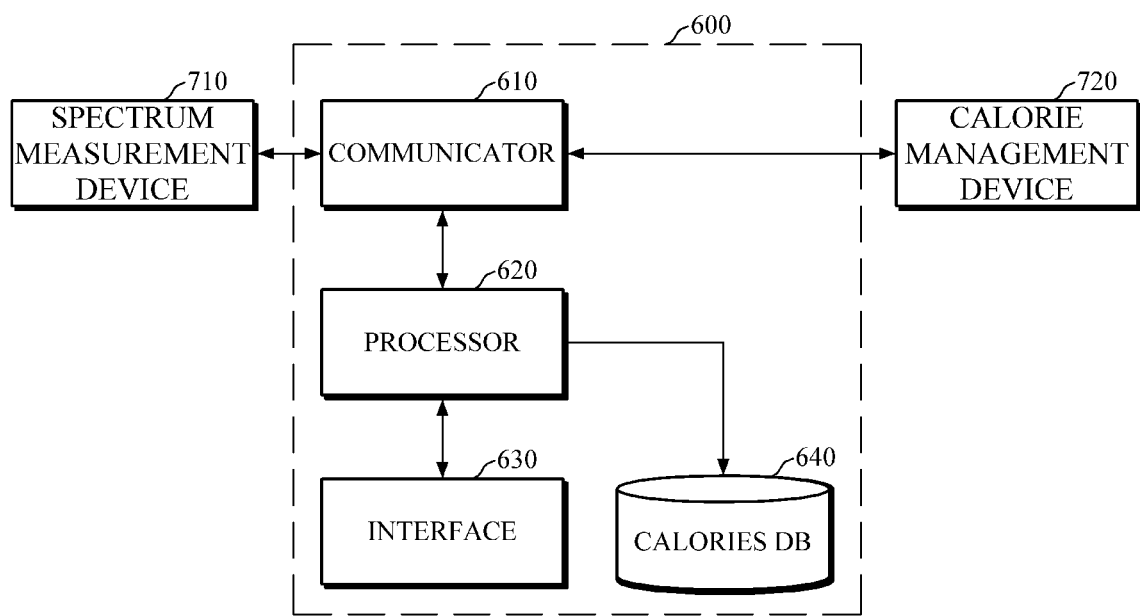
FIG. 6 is a diagram illustrating a calorie estimation apparatus according to another exemplary embodiment.

FIG. 6 is a diagram illustrating a calorie estimation apparatus according to another exemplary embodiment. A calorie estimation apparatus 600 according to an exemplary embodiment may be implemented as software or hardware in mobile terminals, such as smartphones, tablets, PCs, and in various computing devices, which can process data, such as desktop PCs, laptop PCs, etc. However, the calorie estimation apparatus 600 is not limited thereto, and also is not particularly limited in its portability, size, etc.

Referring to FIG. 6, the calorie estimation apparatus 600 may include a communicator, a processor 620, an interface 630, and a storage/memory including a calorie database (DB) 640.

The communicator 610 may communicate with a spectrum measurement device 710, a calories management device 720 managing the calorie information, and other external devices by using communications technology. According to an exemplary embodiment, the communications technology may be the following communications technology: Bluetooth®, Bluetooth low energy (BLE), near-field communication (NFC), a wireless local area network (WLAN) (WiFi), Zigbee, infrared data association (IrDA), Wi-Fi direct (WFD), ultra wideband (UWB), Ant+, WiFi, 3G, 4G, and 5G. However, the communication technology is not limited thereto.

The spectrum measurement device 710 may be a wearable device that a user can wear on the back of his or her wrist, although exemplary embodiments are not limited thereto, and furthermore, exemplary embodiment are not limited to the spectrum measurement device 710 having a small size or portability. For example, the spectrum measurement device 710 may be a device that is fixedly installed in medical institutions, etc., to measure skin spectrums of a plurality of users. The spectrum measurement device 710 may include a communication module that communicates wired or wirelessly, and may communicate with a communicator 610 of the calorie estimation apparatus 600 after a wired connection or an access to wireless communication networks through the communication module.

The spectrum estimation device 710 may measure a user's skin spectrum according to a control signal, thereby acquiring skin spectrum data. For example, the spectrum measurement device 710 may operate a light source in response to a control signal generated by a user operating the control module mounted on the device 710, or in response to a control signal received from the calorie estimation apparatus 600 through the communicator 610, and then may radiate light to a user's skin. Then, the spectrum measurement device 710 may acquire spectrum data by detecting spectral lines of the light that is radiated from the light source and then comes back after being reflected or scattered from a user's skin.

If the spectrum data is acquired, the spectrum measurement device 710 may transmit the acquired spectrum data to the communicator 610 of the calorie estimation apparatus 600 through a communication module.

In addition to a function of measuring the spectrum, the spectrum measurement device 710 may include various additional functions, such as a calorie calculation function, a calorie information output function, and a warning output function like an alarm, according to a size or a computing performance of the device 710.

The calorie management device 720 may manage calorie-related reference information, statistical information, or the like, based on calorie information received from a plurality of users, calorie-related expert knowledge, etc. The calorie management device 720 may be a device, such as a server, which has a relatively excellent computing function, but it is not limited thereto.

For example, the calorie management device 720 may receive calorie information related to users from a plurality of calorie estimation apparatuses 600 that are connected over communications networks. The calorie management device 720 may analyze and add up the received calories information of the users, thereby managing a calorie ingestion history during a regular period of time (e.g., a day, week, month, year, etc.) for each user.

Also, the calorie management device 720 may collect expert knowledge, etc., related to calories. The calorie management device 720 may analyze a correlation, etc., with users' health according to a calorie history by using the collected expert knowledge, etc., and manage comprehensive analysis results and relevant statistical information for each user.

The calorie management device 720 may receive, from a plurality of users, reference spectrum data that is measured in a second condition. Also, the calorie management device 720 may manage a reference spectrum noise for each user or a reference spectrum noise that is applicable in common based on the received reference spectrum of the second condition. According to an exemplary embodiment, the second condition may refer to a condition of an empty stomach as described above, but is not limited thereto as described above.

For example, the calorie management device 720 may manage the reference spectrum noise individually for each user. In this case, when the reference spectrum noise is calculated regarding one user, only the reference spectrum data received from the user may be used. Alternatively, reference spectrum data of other users, who have similar properties with the user (e.g., an age, a sex, a health condition, a usual exercise amount, etc.), may be considered together.

In another example, the calorie management device 720 may manage reference spectrum noise that is applicable in common to all the users. Alternatively, the calorie management device 720 may divide users into a few groups according to user's properties, etc., and manage the reference spectrum noise for each divided group. According to an exemplary embodiment, the calorie management device 720 may select at least a part of users according to a preset criterion among all the users or the users of each divided group, and manage the statistics, such as an average of the noise of the spectrum regarding the selected users, to be a reference spectrum noise that is applicable in common to all the users or each of the groups.

In addition, the calorie management device 720 may build a correlation model that shows a correlation between a spectrum noise and calories by handling the calorie information collected from the users, the expert knowledge, etc., as learning data. According to an exemplary embodiment, the correlation model may be a form of an equation algorithm or a matching table as described above.

In the same fashion as the noise of a reference spectrum, the calorie management device 720 may manage the correlation model by personalizing the correlation model for each of the users. If necessary or desired, the calorie management device 720 may manage the correlation model that is applicable in common to all the users or each group that is divided in predetermined groups.

The communicator 610 may receive the spectrum data of the first condition, which is measured from the user, from the spectrum measurement device 710. According to an exemplary embodiment, the first condition refers to a current condition, in which a user wants to estimate calories as described above, e.g., a condition after the user has had food and drink. However, exemplary embodiments are not limited thereto.

In addition, the communicator 610 may access wired or wireless communications networks and communicate with the calorie management device 720 according to an operation of the processor 620 or automatically in a predetermined point in time, and may receive, from the calorie management device 720, information which is related to a reference spectrum noise or a correlation model that is needed for calorie estimation.

When a user's skin spectrum data for calorie estimation is received, the processor 620 may analyze the received spectrum and calculate a spectrum change, e.g., noise. In addition, if the spectrum noise is calculated, a user's calorie may be estimated based on the calculated noise of the spectrum.

For example, if the spectrum noise of the first condition is calculated based on the received spectrum data, the processor 620 may compare the spectrum noise to the reference spectrum noise, calculate a difference therebetween, and estimate calories by using the difference between the calculated spectrum noises. According to an exemplary embodiment, the processor 620 may calculate a spectrum variation in a plurality of positions of spectrum data wavelengths as illustrated in FIG. 2A, and may use the RMS and the standard deviation of the spectrum variation as the spectrum noise of the first condition.

According to an exemplary embodiment, the processor 620 may estimate calorie information corresponding to a difference between spectrum noises of the first and second conditions by applying the correlation model. If there is a user's input, or a preset time point is reached, the processor 620 may control the communicator 610 to receive correlation model information from the calorie management device 720, and when the correlation model information is received, may update the existing correlation model information.

When a user's calories are estimated, the processor 620 may store the estimated calorie information in the calorie DB 640, and update calorie history information. Additionally, the processor 620 may generate all kinds of information regarding a user's healthcare based on the user's calorie history information, and manage such all kinds of information in the calorie DB 640.

The processor 620 may transmit calorie information and all kinds of generated information to the calorie management device 720 through the communicator 610, so that the calorie management device 720 may build the user's calorie information and calorie-related knowledge.

The interface 630 may interact with a user through an interface module that is connected to or mounted on the calorie estimation device 600. According to an exemplary embodiment, the interface module may include a display, a microphone, a speaker, a haptic device, etc., but exemplary embodiments are not limited thereto.

The interface 630 may show a graphic user interface (GUI) on a display so that a user may input a control command through a touch input. If the user inputs a control command for calorie estimation through the GUI, the interface 630 may transmit the input control command to the processor 620.

The interface 630 may provide the user with all kinds of information, such as a processing result of the processor 620, an alarm, a warning, etc., in a visual way of displaying the information on a display, or in an auditory way of emitting sound through a speaker. In addition, if a haptic device is connected, the interface 630 may use various non-visual or audio ways, such as vibration, touch, pressure, etc. According to an exemplary embodiment, the haptic device may be a device in a ring or band form, which is wearable on a finger or wrist, but exemplary embodiments are not limited thereto.

For example, if a user's calories are estimated by the processor 620, the interface 630 may determine a level of the estimated calories according to a preset criterion. Also, the interface 630 may provide a user with additional information, such as estimated calories, warning, alarm, etc., in a way that corresponds to the determined level. For example, as shown in Table 3, the calorie level may be set in advance to be a plurality of levels according to a calorie range for each user. In addition, ways of providing information to a user may be set differently according to each calorie level, such as display color, number of times being vibrated, vibration intensity, pressure intensity, etc.

According to an exemplary embodiment, the preset criterion may be divided into a plurality of calorie ranges based on a recommended calorie intake that is applicable in common, and may be set to be a plurality of stages (e.g., below, normal, above). Alternatively, the preset criterion may be set to be appropriate for a user by adjusting a one-time calorie intake, a daily calorie intake, a monthly calorie intake, etc., or by adjusting a calorie range of each stage for the user according to the user's normal health condition, a purpose of being on a diet, etc.

TABLE 3

| Calorie level | Color | Number of vibration times |
|---|---|---|
| Below | Yellow | Once |
| Normal | Green | Twice |
| Above | Red | Three times |

In a case where a user inputs a calorie estimation command or a request for all kinds of information with voice using a microphone, the interface 630 may transmit the input voice to the processor 620. According to an exemplary embodiment, the processor 620 may perform voice recognition by using a voice recognition technology, then analyze the voice recognition result, and process an operation corresponding to the analysis result.

If a user's request for information provision related to calories is received from the interface 630, the processor 620 may control the communicator 610 to be connected to the calorie management device 720, receive the corresponding information from the calorie management device 720, and provide the information to a user through the interface 630.

If a user directly controls the spectrum measurement device 710 so as to request a spectrum measurement and a calorie estimation, if it is impossible for the calorie estimation device 600 to directly provide calorie information to a user because the calorie estimation device 600 is located in a remote area from a user, or if there is a user's request, the processor 620 may control the communicator 610 so that the spectrum measurement device 710 may provide calorie information, etc., to a user, and transmit estimated calorie information, etc., to the spectrum measurement device 710.

Figure 7:
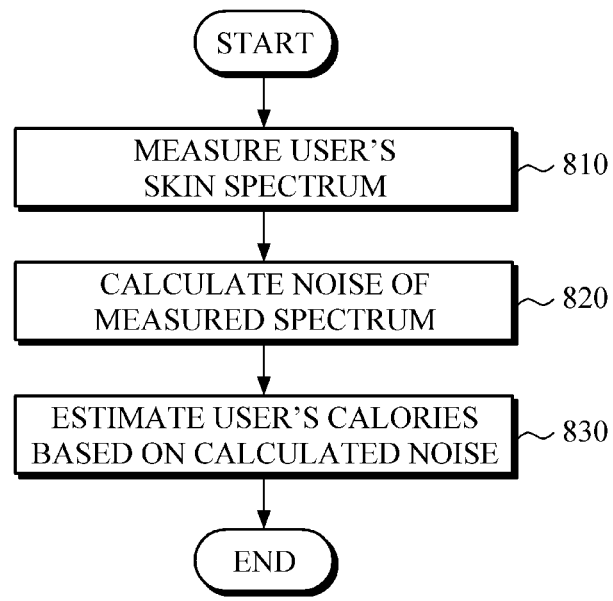
FIG. 7 is a flowchart illustrating a calorie estimation method according to an exemplary embodiment.
Figure 8:
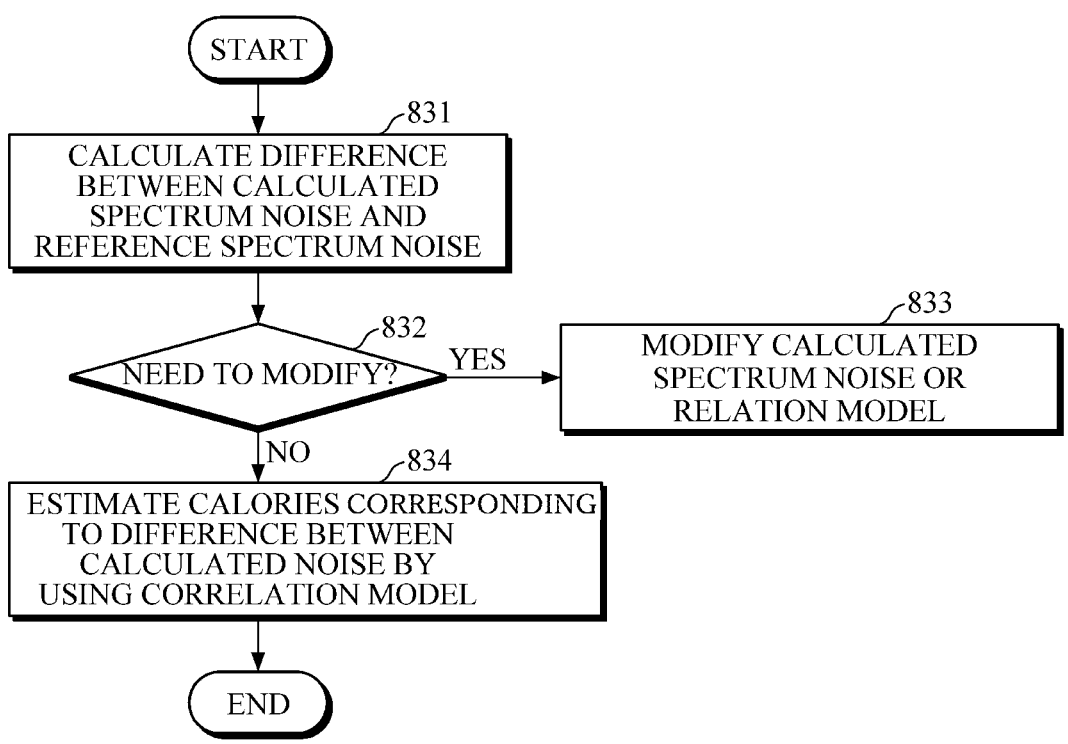
FIG. 8 is a detailed flowchart illustrating a calorie estimation operation in FIG. 7 according to an exemplary embodiment.

FIG. 7 is a flowchart illustrating a calorie estimation method according to an exemplary embodiment. FIG. 8 is a detailed flowchart illustrating a calorie estimation operation 830 in FIG. 7 according to an exemplary embodiment.

Referring to FIGS. 7 and 8, an exemplary embodiment of a calorie estimation method, which is performed by a calorie estimation apparatus 100, is illustrated. Referring to FIGS. 1 to 5, certain exemplary embodiments of a calorie estimation method that the calorie estimation apparatus 100 performs are specifically described above. Thus, the method shown in FIGS. 7 and 8 will be described simply to avoid repetition.

First, a user's skin spectrum may be measured in a first condition where a user wants to estimate calories in operation 810. The calorie estimation apparatus 100 may radiate light to a user's skin in response to a predetermined control signal, analyze the light coming back from the skin, and acquire the spectrum data. According to an exemplary embodiment, Raman spectroscopy or Infrared spectroscopy may be used, but exemplary embodiments are not limited thereto.

Next, if a skin spectrum of the first condition regarding a user is measured in operation 810, a noise of the measured skin spectrum may be calculated in operation 820. For example, a spectrum variation may be calculated in a plurality of wavelength positions of the measured spectrum data, and the RMS or the standard deviation of the calculated spectrum variation may be calculated as a noise of the spectrum.

Next, if the spectrum noise of the first condition is calculated, a user's calories may be estimated based on the calculated spectrum noise in operation 830.

Referring to FIG. 8, according to an exemplary embodiment of operation 830, after the spectrum noise of the first condition is first calculated in operation 820, a difference between the calculated spectrum noise of the first condition and a reference spectrum noise of the second condition may be calculated in operation 831.

Next, if necessary, the calorie estimation apparatus 100 may determine whether information required for calorie estimation should be modified in operation 832. That is, a calorie intake of food and drink that a user has actually ingested, and a calorie amount absorbed inside the user's body may be different according to a user's health condition, etc. As such, if a user wants to know not the calorie amount absorbed inside the body, but the calorie intake of food and drink that the user has actually ingested, a criterion for calorie estimation or a modification of the estimated calories itself may be required.

For example, the calorie estimation apparatus 100 may determine whether the modification of the estimated calories is needed, based on a user's health condition information, calorie consumption information, or the like, which affects calorie calculation. According to an exemplary embodiment, the health condition information may be factors that affect the calorie calculation in the longer term, such as a user's age, diseases, unusual constitution, etc., as described above. In addition, the calorie consumption information may be factors that temporarily affect calorie calculation at the point in time when calories are to be estimated, such as whether a user has exercised, an amount of exercise, an exercise intensity, exercise times, etc.

If it is determined that the modification is required, the calorie estimation apparatus 100 may acquire a correlation between calories of food and drink that a user has actually ingested and the estimated calories. By using the acquired result, the calorie estimation apparatus 100 may modify the correlation model or the difference of the calculated spectrum noise so that the estimated calories may come closer to the calories of food and drink that are actually ingested in operation 833.

Next, after the noise difference between the spectrums is calculated in operation 831, or after the information that is a criterion is modified in operation 833, a user's calories may be estimated based on the result in operation 834. The calorie estimation apparatus 100 may estimate calories by using a pre-built correlation model. According to an exemplary embodiment, the correlation model may be an equation algorithm, or may be a table, where spectrum noise differences and calories are matched, as shown in FIG. 4 and Table 1. For example, assuming that a difference between a spectrum noise calculated in the first condition and a reference spectrum noise is 4100 μAU, if a correlation model of FIG. 4 is applied, the calories may be estimated as 284.95 (4.1=0.8167x−49.1) kcal.

For example, the calorie estimation apparatus 100 may repeatedly perform an operation of measuring a spectrum that is above a predetermined criterion in first and second conditions, handle the plurality of measured spectrum data as learning data, acquire a difference between the spectrum noises of the first and second conditions, and a correlation with calories, and build the correlation model. In another example, the calorie estimation apparatus 100 may use a basic correlation model that is included in the calorie estimation apparatus 100, and may receive a correlation model from other external devices.

Operations 832 and 833 may be performed according to the operations specifically described with reference to FIG. 5. Thus, a specific description of operations 832 and 833 is omitted. Operations 832 and 833 are not considered to be necessary in the calorie estimation method, and may thus be omitted according to the purpose of use, the computing performance of the apparatus 100, etc. In addition, operations 832 and 833 may be performed after operation 834. In this case, if the calories are estimated in operation 834, the calorie estimation apparatus 100 may determine whether the modification of the estimated calories is required in 832. Based on the determination result 832, the calorie estimation apparatus 100 may modify the estimated calories itself in operation 833 if the amendment of the calories is required.

Figure 9:
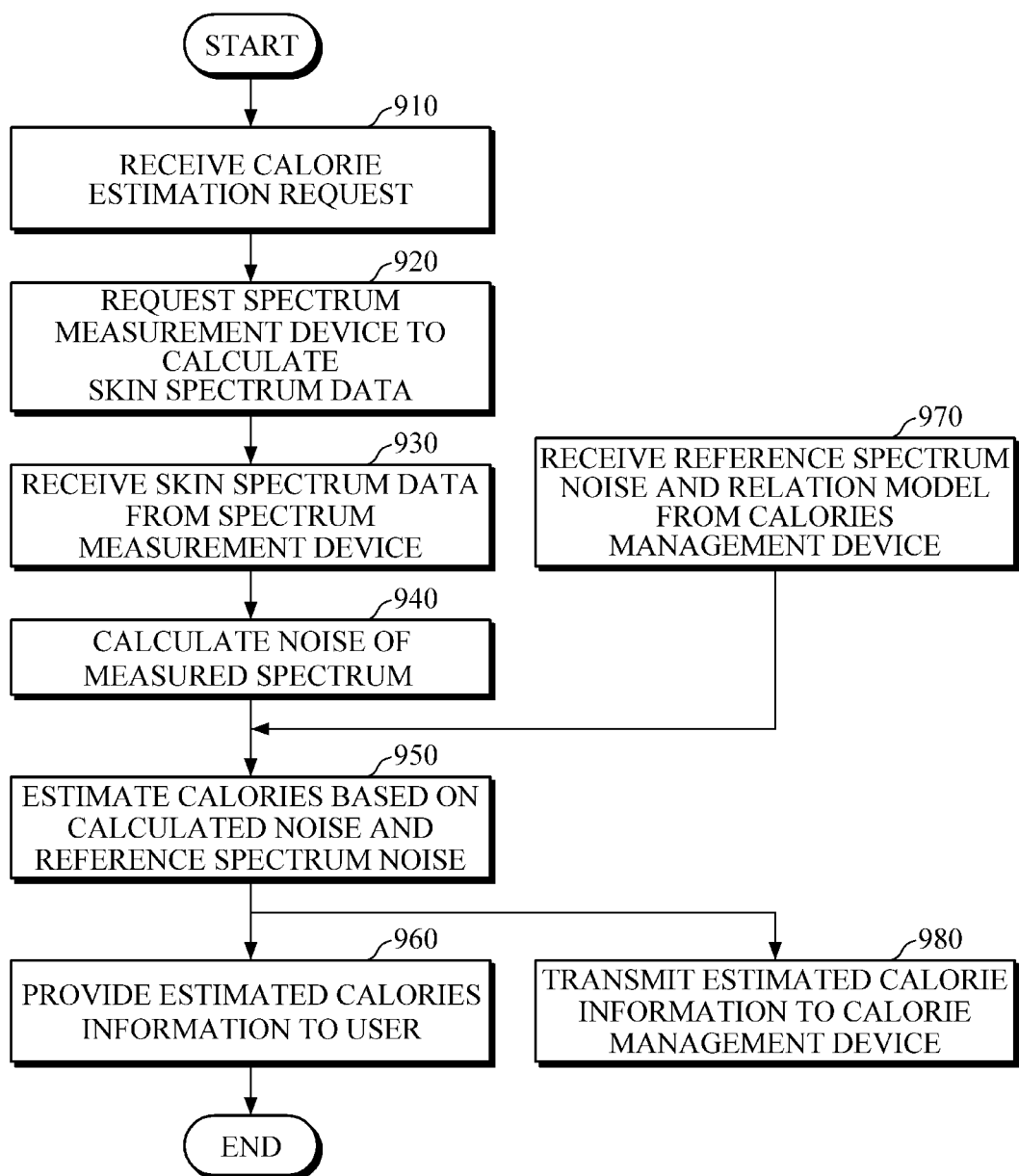
FIG. 9 is a flowchart illustrating a calorie estimation method according to another exemplary embodiment.

FIG. 9 is a flowchart illustrating a calorie estimation method according to another exemplary embodiment.

Referring to FIG. 9, an exemplary embodiment of a calorie estimation method that a calorie estimation apparatus 600 performs is described. However, the exemplary embodiment of the calorie estimation method that the calorie estimation apparatus 600 performs is specifically described above with reference too FIG. 6. Thus, the method of FIG. 9 will be described simply to avoid repletion.

First, the calorie estimation apparatus 600 may receive a calorie estimation request from a user in operation 910. According to an exemplary embodiment, the calorie estimation apparatus 600 may receive a control command regarding the calorie estimation request that is input by the user through a connected interface module, e.g., display, a microphone, etc.

Next, the calorie estimation apparatus 600 may transmit a control signal to a spectrum measurement device, by which the calorie estimation apparatus 600 requests the spectrum measurement device to measure a user's skin spectrum in operation 920.

However, a user may directly control the spectrum measurement device to measure a spectrum, and in this case, operations 910 and 920 may be omitted.

Next, a user's skin spectrum data may be received from the spectrum measurement device in 930.

Next, after the user's skin spectrum is received, a noise may be calculated from the received skin spectrum of the user in operation 940. For example, the calorie estimation apparatus 600 may calculate a spectrum variation in a plurality of wavelength positions of the received spectrum data as described above, and may calculate the RMS or the standard deviation of the calculated spectrum variation as a noise of the spectrum.

Next, the calorie estimation apparatus 600 may estimate calories by using the spectrum noise calculated in operation 940 and the reference spectrum noise in operation 950. For example, the calorie estimation apparatus 600 may calculate a difference between the noise, calculated in operation 940, and the reference spectrum noise, and estimate the calories by using the difference of the calculated spectrum noise and the correlation model in 950. If the correlation model is an equation algorithm, the calories may be acquired by putting the difference of the spectrum noise to the equation algorithm. If the correlation model is a matching table, the calories corresponding to the spectrum noise difference may be acquired from the matching table.

Next, the estimated calorie information may be provided to a user in operation 960. According to an exemplary embodiment, the calorie estimation apparatus 600 may determine a level regarding the estimated calories, and provide the calorie information to a user in a way that corresponds to the determined level. For example, the calorie level may be set for each user or for each of the plurality of intervals of a calorie range that is applicable in common. A display color, vibration times, vibration intensity, a pressure intensity, etc. may be set differently according to each level. According to an exemplary embodiment, the information may be provided the user according to a connected interface module in various ways of visual, tactile, auditory, pressure senses, etc.

In order to update a noise of the existing reference spectrum or a correlation model, the calorie estimation apparatus 600 may communicate with the calorie management apparatus periodically or in response to a user's request, etc., thereby receiving the reference spectrum noise information or the correlation model (e.g., relation model) information in operation 970.

Also, the calorie estimation apparatus 600 may transmit the estimated calorie information to the calorie management apparatus, so that the calorie management apparatus may perform re-training, etc., of the correlation model in operation 980.

However, operations 970 and 980 are not considered to be necessary in the calorie estimation method according to an exemplary embodiment, and may thus be omitted according to the needs or desires of a user.

Figure 10:
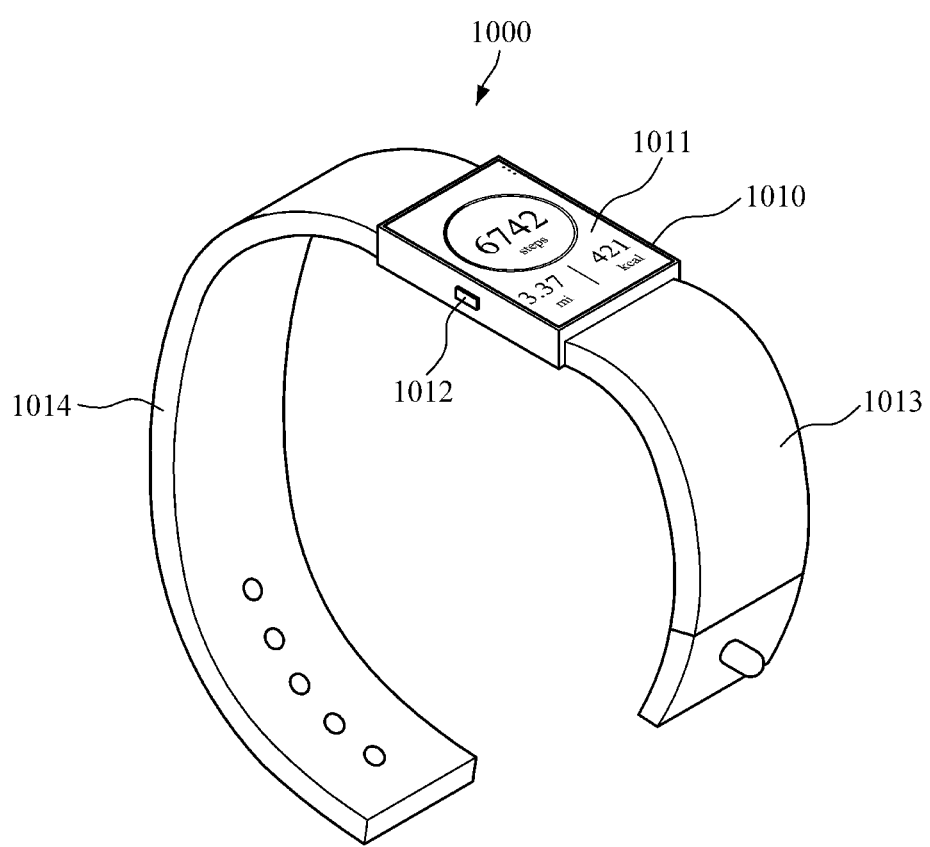
FIG. 10 is a perspective view of a wearable device according to an exemplary embodiment.
Figure 11:
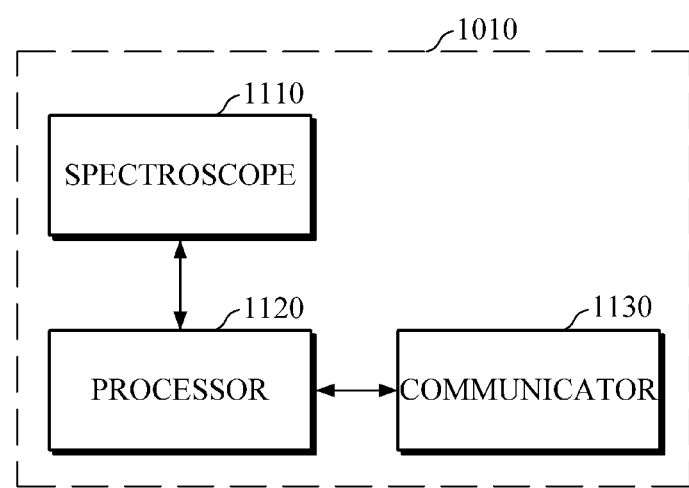
FIG. 11 is a diagram illustrating an element mounted on the main body of a wearable device in FIG. 10.

FIG. 10 is a perspective view of a wearable device according to an exemplary embodiment. FIG. 11 is a diagram illustrating an element mounted on the main body of a wearable device in FIG. 10. Various exemplary embodiments of the calorie estimation apparatus described above, as illustrated in FIGS. 10 and 11, may be mounted on a smart band-type wearable device. However, since this is only one example for convenience of description, exemplary embodiments herein should not be construed as being limited to the smart band-type wearable device.

Referring to FIGS. 10 and 11, a wearable device 1000 may include a main body 1010 and a strap including strap members 1013 and 1014.

The strap may be flexible and thus capable of bending so as to wrap around or unwrap from a user's wrist. According to an exemplary embodiment, the main body 1010 or the strap member 1014 may include a battery inside to provide power to the wearable device.

Also, the main body 1010 of the wearable device 1000 may include, in an internal space, a spectroscope 1110, which radiates light to a user's skin and detects spectral lines of the light that comes back after being scattered or reflected from the user's skin so as to measure a spectrum, and a processor 1120 that estimates the user's calories by using the spectrum measured by the spectroscope 1110.

The spectroscope 1110 may operate a light source in response to a control signal of the processor 1120, radiate light to a user's skin, and disperse the light that returns after traveling into the user's skin. Specifically, the light radiated from the light source travels into the user's skin and reaches the biological tissues, and the light that has reached the biological tissues returns after reacting with the biological tissues. The spectroscope 1110 may acquire a spectrum of the returning light, which is then transmitted to the processor 1120. According to an exemplary embodiment, the light source may radiate light of near-infrared or mid-infrared region.

Also, the spectroscope 1110 may include a linear variable filter (LVF). An LVF has spectral properties that vary linearly from one end of the LVF to the other end of the LVF. The LVF has a spectrum that is changed in a linear form throughout the entire length of the LVF. Thus, the LVF can disperse an incident ray into a spectrum according to the order of wavelength. Though an LVF is compact in size, the LVF has powerful spectral capability.

The processor 1120 may generate a control signal in response to a user's calorie estimation request, thereby controlling the spectroscope 1110. Also, after the spectroscope 1110 acquires the skin spectrum from a user, the user's skin spectrum data may be received from the spectroscope 1110. Also, after the spectrum data is received from the spectroscope 1110, the processor 1120 may estimate the user's calories by using the received spectrum data. For example, the processor 1120 may calculate a noise of the received skin spectrum, and once the noise is calculated, such noise is compared to the noise that is calculated from the existing spectrum. The difference between both spectrum noises is applied to a correlation model so that the calories may then be estimated.

Also, based on the estimated calorie information, the processor 1120 may generate additional information required for a user's healthcare, such as warning or alarm information about calorie excess or deficiency, a health condition change, etc.

The wearable device 1000 may further include an adjuster 1012 mounted on the main body, and a display 1011.

The adjuster 1012 may receive a user's control command and transmit the control command to the processor 1120, and may include a power button for inputting a command to turn on/off the power of the wearable device 1000.

The display 1011 may display additional information, such as the calorie information that is estimated according to the control by the processor 1120, a warning, alarm, etc., thereby providing such information to a user. According to an exemplary embodiment, the display 1011 may show a user the additional information, such as the calorie information, alarm, warning, etc., by using various visual methods.

In addition, the main body 1010 may additionally include a communicator 1130 for communicating with other external devices, such as user's mobile terminal, a calorie management device, etc.

According to a control by the processor 1120, the communicator 1130 may transmit information to a user's mobile terminal, whose computing performance is relatively outstanding, and the mobile terminal may then provide the information to a user. Also, in connection with the calorie management device, the communicator 1130 may receive, from the calorie management device, correlation model information required for calorie estimation, or reference spectrum noise information, etc., thereby updating the existing information.

The methods and/or operations described above may be recorded, stored, or fixed in one or more non-transitory computer-readable storage media that includes program instructions to be implemented by a computer to cause a processor to execute or perform the program instructions. The media may also include, alone or in combination with the program instructions, data files, data structures, and the like. Examples of computer-readable storage media include magnetic media, such as hard disks, floppy disks, and magnetic tape, optical media such as CD ROM disks and DVDs, magneto-optical media, such as optical disks, and hardware devices that are specially configured to store and perform program instructions, such as read-only memory (ROM), random access memory (RAM), flash memory, and the like. Examples of program instructions include machine code, such as code generated by a compiler, and files containing higher level code that may be executed by the computer using an interpreter. The described hardware devices may be configured to act as one or more software modules in order to perform the operations and methods described above, or vice versa. In addition, a computer-readable storage medium may be distributed among computer systems connected through a network and computer-readable codes or program instructions may be stored and executed in a decentralized manner.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A wearable device comprising:
   a main body;
   a spectroscope that is included in the main body, the spectroscope being configured to radiate light to skin of a user, detect spectral lines of the light that is reflected or scattered from the skin, and measure a skin spectrum based on the detected spectral lines;
   a processor configured to determine a noise of the measured skin spectrum and a difference between the determined noise and a reference spectrum noise; and
   estimate calories consumed by the user based on the determined difference between the determined noise and the reference spectrum noise by using a correlation model correlating a predefined noise and calories.

2. The wearable device of claim 1, further comprising a communicator, which is included in the main body, and configured to communicate with a calorie management device so as to receive at least one of the reference spectrum noise and a correlation model to be used for estimating the calories.

3. The wearable device of claim 1, further comprising a display that is mounted on the main body so as to show the user the calories that are estimated by the processor.

* * * * *